United States Patent
Jinnouchi

(10) Patent No.: US 6,276,932 B1
(45) Date of Patent: Aug. 21, 2001

(54) ARCH WIRE, METHOD FOR PREPARING THE ARCH WIRE AND SPHERICAL PLATE THEREFOR

(75) Inventor: Hiroshi Jinnouchi, 159 Nanashima-cho, Kanagawa-ku, Yokohama-shi, Kanagawa (JP)

(73) Assignees: Hiroshi Jinnouchi; Keiko Jinnouchi, both of Yokohama-shi (JP)

( * ) Notice: Subject to any disclaimer, the term of this patent is extended or adjusted under 35 U.S.C. 154(b) by 0 days.

(21) Appl. No.: 09/577,933

(22) Filed: May 25, 2000

(30) Foreign Application Priority Data

May 27, 1999 (JP) .................................... 11-147658

(51) Int. Cl.[7] ....................................... A61C 3/00

(52) U.S. Cl. ............................... 433/20; 433/72

(58) Field of Search ........................ 433/20, 72

(56) References Cited

U.S. PATENT DOCUMENTS

| | | | | |
|---|---|---|---|---|
| 4,097,993 | * | 7/1978 | Andrews ................................ | 433/20 |
| 4,818,226 | * | 4/1989 | Berendt et al. ......................... | 433/20 |
| 5,092,941 | * | 3/1992 | Miura ..................................... | 433/20 |
| 5,137,446 | * | 8/1992 | Yamauchi et al. ...................... | 433/20 |

* cited by examiner

*Primary Examiner*—Nicholas D. Lucchesi
(74) *Attorney, Agent, or Firm*—Armstrong, Westerman, Hattori, McLeland & Naughton, LLP

(57) ABSTRACT

Monson spherical plate has an arch chart drawn thereon for preparing an arch wire. A maxillary dental arch curve and a mandibular dental arch curve are drawn on concave and convex surfaces of a Monson spherical plate and an arch wire afforded with a Monson curve is prepared along this arch curve. It is possible to inhibit Christensen phenomenon and changes in the curve of occlusion and to smooth muscle movements around the mandible. An arch wire having a curve corresponding to the curve of occlusion can be prepared using the Monson spherical plate.

18 Claims, 4 Drawing Sheets

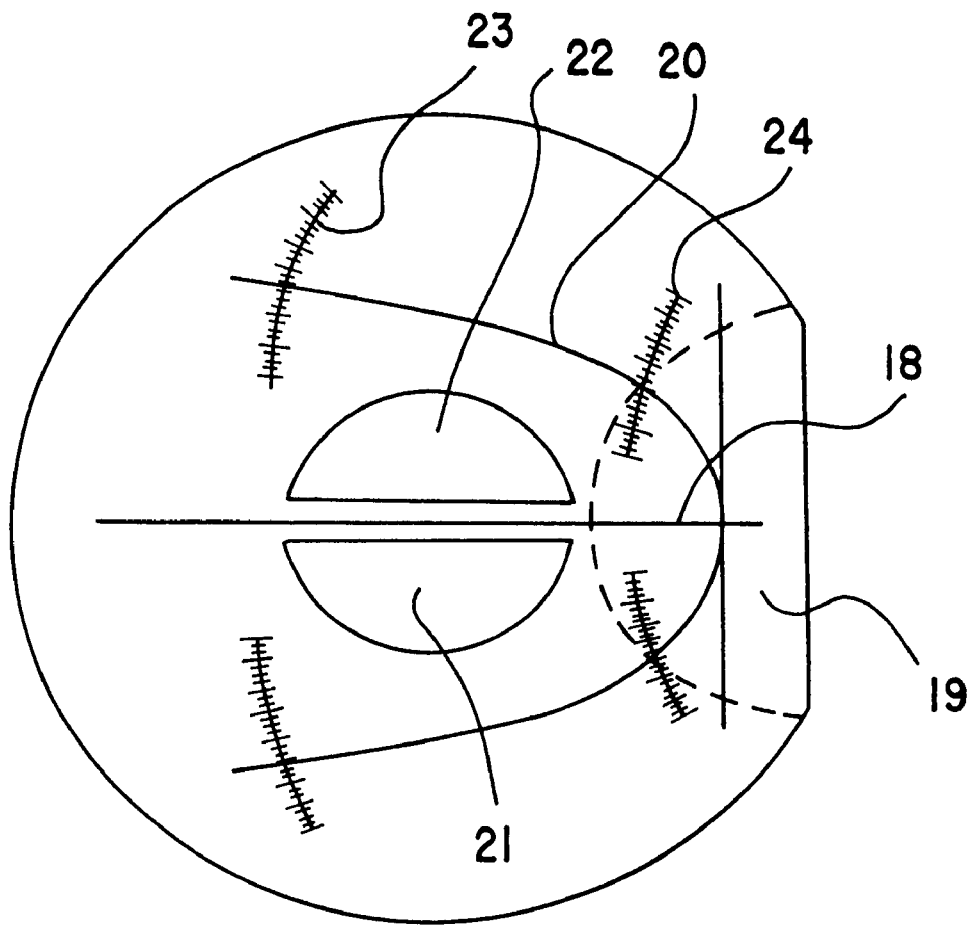

ARCH WIRE, METHOD FOR PREPARING THE ARCH WIRE AND SPHERICAL PLATE THEREFOR

FIELD OF THE INVENTION

This invention relates to an arch wire corresponding to a curve of an occlusal surface of a dental arch and a spherical plate for preparing the arch wire. More particularly, it relates to a Monson spherical plate for preparing an arch wire afforded with a Monson curve for bending and shaping used for preventing collapsing of the curve of Spee of a dental arch of each patient receiving corrective full-band treatment. The present invention also relates to an arch wire prepared using such a spherical plate, a method for preparing the arch wire and, more broadly, to a corrective treatment of a dental arch.

BACKGROUND OF THE INVENTION

In the conventional corrective full-band treatment, an arch wire was prepared by warping a wire along a dental arch in a plan view, placing emphasis only on aesthetic aspects, with respective teeth being arrayed flatly in an elevational view.

SUMMARY OF THE DISCLOSURE

There is much to be desired in the art and the following problems have been encountered during the investigations toward the present invention.

In such treatment, since the respective teeth are arrayed flatly in the elevational view, there is presented a problem that manifestation of the Christensen phenomenon, impeded motion of muscles around the jaws, or an excess pressure is apt to be applied to the teeth due to flattening of the curve of occlusion.

In view of the above-mentioned problems of the related art, it is an object of the present invention to provide a Monson spherical plate having drawn thereon an arch chart for preparing an arch wire whereby it is possible to prevent the Christensen phenomenon, assure a smooth motion of muscles around the jaws and to prevent the curve (surface) of occlusion from being changed.

In another aspect, it is an object of the present invention to provide an arch wire having a curvature corresponding to the curved surface of occlusion and a method for preparing same.

For accomplishing the above object, the present invention provides, in its first aspect, a Monson spherical plate on which are drawn a dental arch curve, scales and an arch reference line usable for preparing an arch wire.

In the present invention, the "Monson spherical plate" means a substantially spherically shaped plate member having a substantially spherical surface (or a portion of the spherical surface) corresponding to a curve of the occlusal surface of the dental arch. Theoretically, the curve of occlusion is called a Monson curve. So, in the present invention, an imaginary spherical surface containing this Monson curve is called a "Monson sphere" and the "Monson spherical plate" is correspondingly denominated. The diameter or the size is, however, suitably changed to conform to the status of the teeth of a patient being corrected, without being constrained by this definition.

Meanwhile, the theoretical "Monson curve" is defined as "a sort of a compensating curve derived from the theory on a spherical surface concerned with jaw movements of G. S. Monson and forms a spherical surface 8 inch in diameter, with an inch corresponding to approximately 2.54 cm", ENCYCLOPAEDIA DENTALIS, Jul. 20, 1976 first Edition, Nagasue Shoten, page 703. In this publication, there is a description which runs; "It is in actuality like a timepiece saucer of metal with a diameter of 8 inch. It first applies a compensating curve to an occlusion rim which is a portion of a spherical surface with the center lying in the glabella (ethmoid crista galli). A set of artificial teeth is arrayed so that its margo incisalis (incisal margin) and both buccolingual cusps contact the spherical surface. By arraying the set of artificial teeth in this manner, it is possible to realize a balanced occlusion so that the artificial teeth will extend along the condyle path upon the mandible movement in case of the full denture" (ibid). The theory of Monson sphere is "the theory of an imaginary jaw movement publicized by Monson in 1920" (ibid). There is also a description which runs; "In a well-grown mandible, the condile, margo incisalis of anterior teeth and buccolingual side cusps of the molar teeth are arranged on a sole spherical surface, with the mandible movements occurring as a sliding movement along this spherical surface. The long axis of each tooth is directed to the center of this sphere, with the center lying on a median line in the ethmoid crista galli, with the radius being said to be 4 inch on an average" (ibid).

Means for accomplishing the above object in further aspects of the present invention are now enumerated.

In a second aspect of the present invention, an arch chart comprising a maxillary (upper jaw) dental arch curve, scales and an arch reference line is preferably drawn in a concave surface of the Monson spherical plate and a portion thereof engaged by anterior teeth has a planar portion.

In a third aspect of the present invention, an arch chart comprising a mandiblar dental arch curve, scales and an arch reference line is preferably drawn on a convex surface of the Monson spherical plate and a portion thereof engaged by the anterior teeth has a planar portion.

In a fourth aspect of the present invention, legs are preferably provided on the bottom of the Monson spherical plate.

In a fifth aspect of the present invention, when seen in a projection view as seen from the center of sphere of the Monson spherical plate, the dental arch curve is formed preferably by drawing a curve along the contour of the outer side (buccal and labial side) of the dental arch so that the axis of symmetry of the curve traverses the center of the Monson spherical plate.

In a sixth aspect of the present invention, when seen in a projection view as seen from the center of sphere of the Monson spherical plate, the arch reference line preferably comprising an axis of symmetry of the dental arch curve and a tangential line drawn to an apex point of the dental arch curve.

In a seventh aspect of the present invention, when seen in a projection view as seen from the center of sphere of the Monson spherical plate, the scales preferably include a straight line interconnecting center points of left and right canines and a straight line connecting center points of the left and right first molar teeth.

In an eighth aspect of the present invention, when seen in a projection view as seen from the center of sphere of the Monson spherical plate, the planar portion preferably has, as its contour, a curve an axis of symmetry of which coincides with the axis of the dental arch curve and the direction of which is opposite to that of the dental arch curve, with points of intersection of the curve with the dental arch curve substantially coinciding with the positions of left and right canines.

In a ninth aspect of the present invention, the Monson spherical plate preferably has a radius of curvature equal to a reference size or to a variety of sizes different therefrom.

In a tenth aspect of the present invention, the Monson spherical plate has a spherical surface corresponding to a curve of an occlusal surface of a dental arch. Preferably, at least a portion of the plate engaged by anterior teeth is formed as a planar portion.

In an eleventh aspect of the present invention,, the Monson spherical plate preferably has a dental arch curve (curves) and scales on one of both of concave and convex surfaces of Monson spherical plate.

In a twelfth aspect of the present invention, the Monson spherical plate preferably includes an arch reference line constituting an axis of symmetry of dental arch curve on one of both of concave and convex surfaces of Monson spherical plate, with the scales being formed in a direction perpendicular to arch reference line.

In a thirteenth aspect of the present invention,, a method for preparing an arch wire includes using Monson spherical plate as defined above and forming a curve of the occlusal surface corresponding to the dental arch curve(curves) in an arch wire.

In a fourteenth aspect of the present invention, an arch wire conforming to the above object is prepared by the above-defined method.

In a fifteenth aspect of the present invention, an arch wire conforming to the above object has a planar projection shape substantially corresponding to the planar projection shape of a dental arch, that is a curve corresponding to the curve of the occlusal surface (Monson curve) of the dental arch in a spherical surface of the Monson spherical plate.

In a sixteenth aspect of the present invention, the arch wire can be formed of a shape memory alloy, stainless steel or other materials for dental application.

In a seventeenth aspect of the present invention, although such Monson spherical plate on which a standard arch chart or an arch chart of various standard grades is depicted in advance may be used, it is also possible to use a blank Monson spherical plate having no arch chart at the outset, wherein the positions of reference teeth may be specified (depicted) from an individual pattern of teeth in using the Monson spherical plate.

In an eighteenth aspect of the present invention, the scales may be plotted so that, at a point of intersection of the scale with dental arch curve at the left and right first molar teeth and at a point of intersection with left and right canines, a tangential line drawn to the scale at each point of intersection is substantially perpendicular to a tangential line drawn to the dental arch curve.

BRIEF DESCRIPTION OF THE DRAWINGS

FIG. 8 is a top plan view of a convex Monson spherical plate, having a dental arch chart drawn thereon, according to another embodiment.

PREFERRED EMBODIMENTS OF THE INVENTION

Figure 1:
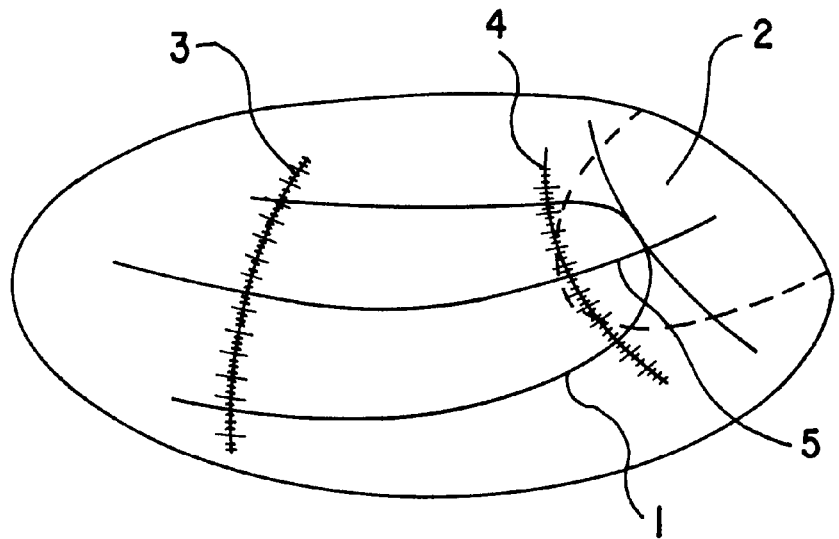
FIG. 1 is a perspective view showing a concave Monson spherical plate having a dental arch chart drawn thereon.

In a concave surface of a Monson spherical plate are drawn an arch chart comprised of maxillary (upper jaw) dental arch curve, a scale and an arch reference line. For an arch chart, a variety of arch charts (that is those representing typical occlusal curved surface for men and women, people of different races, such as white, or colored people) are preferably prepared in advance. Meanwhile, an arch chart for a concave arch chart is to be smaller than an arch chart of a convex surface.

In a convex surface of a Monson spherical plate, an arch chart made up of a mandibular (lower jaw) dental arch curve, a scale and an arch reference line are drawn. A variety of arch charts of concave and convex surfaces are preferably prepared in advance. More specifically, arch charts of a mean (reference) size and sizes slightly larger or smaller than it (i.e., of various grades) are preferably provided in advance.

The portion of the Monson spherical plate engaged by anterior teeth is formed as a planar portion. The area of the planar portion contacted by the anterior teeth is planar when the Monson spherical plate is seen from the front side. That is, the anterior teeth are arrayed horizontally. This gives an aesthetic effect in that the anterior teeth are arrayed horizontally to give an apparently beautiful array of the anterior teeth.

The bottom of the convex surface is preferably provided with legs as a tool for preventing rolling upon being placed on a table etc. It is noted that this embodiment is merely illustrative since it is only sufficient if a similar function is displayed.

The scale is drawn in each of the arched distal (foremost) part of the dental arch curve and the opened both ends of the arch.

The arch reference line is formed, preferably, so as to include at least a symmetrical axis of the arch so that a horizontal line of the curved distal end of the dental arch curve and a vertical line at the center of the arch intersect at right angles with each other.

A wire is warped along the arch curve drawn on the Monson spherical plate to prepare an arch wire. This gives an arch wire having a curvature corresponding to the curve of the occlusal surface, sometimes called a Monson curve.

The arch wire may be provided in advance with a curve in meeting with the curved surface of the Monson spherical plate relative to the Monson curve of the occlusal surface.

DETAILED DESCRIPTION OF THE PREFERRED EMBODIMENTS

Referring to the drawings, preferred embodiments of the present invention will be explained in detail.

Figure 2:
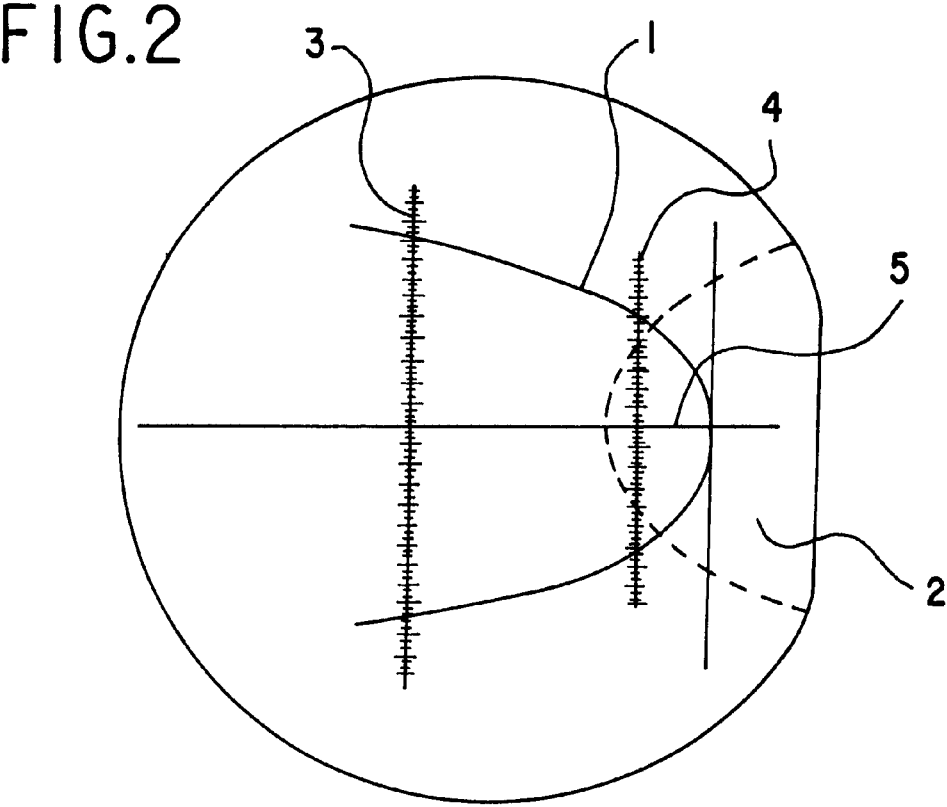
FIG. 2 is an upper surface of a concave Monson spherical plate having a dental arch chart drawn thereon.

Referring to FIGS. 1 and 2, an arch 1 is drawn at a mid portion of a concave surface of a Monson spherical plate, while scales 3, 4 are drawn in upper and lower portions of the arch 1, respectively. An arch reference line 5 is drawn at a mid portion of the distal end of the arch 1 at a median position between both extreme ends of the arch 1. A arch chart is prepared and a portion 2 of the Monson spherical plate engaged by the anterior teeth is formed as a flat portion.

Figure 3:
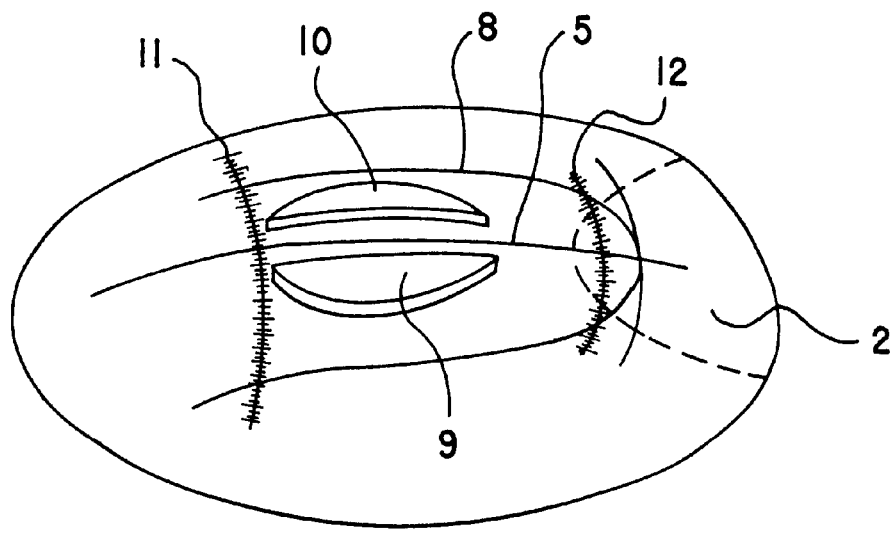
FIG. 3 is a perspective view showing a convex Monson spherical plate having a dental arch chart drawn thereon.
Figure 4:
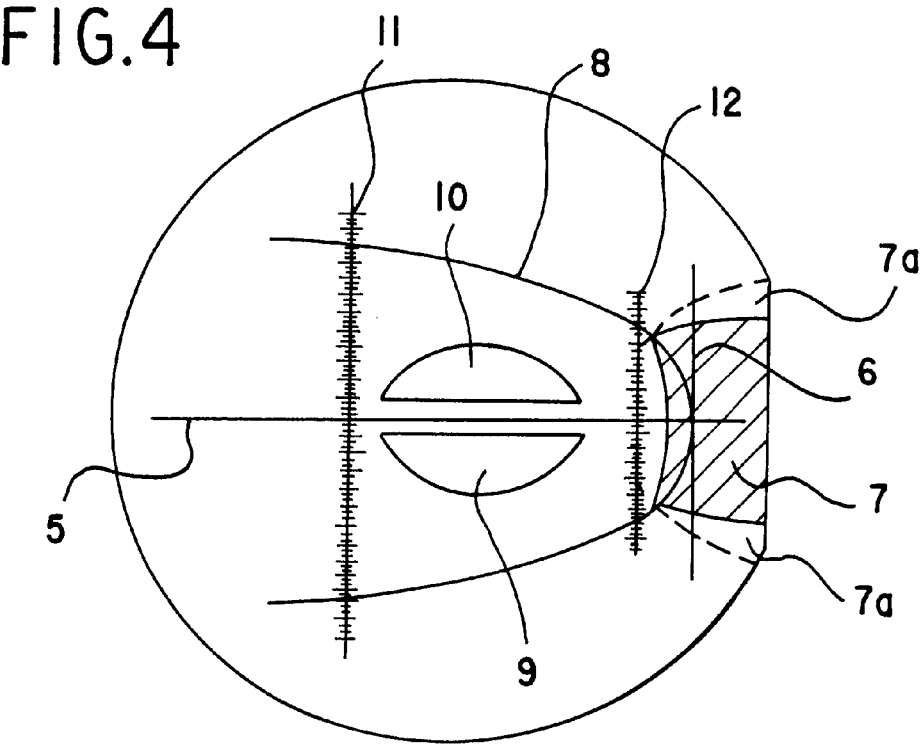
FIG. 4 is a top plan view showing a convex Monson spherical plate having a dental arch chart drawn thereon.
Figure 5:
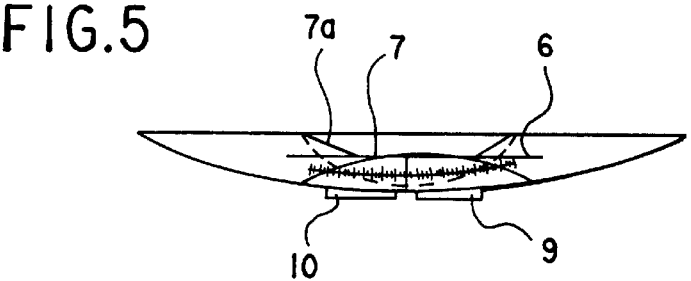
FIG. 5 is a side view, looking from the distal end of the arch, of the convex Monson spherical plate having a dental arch chart drawn thereon, with the convex surface facing downwards.
Figure 6:
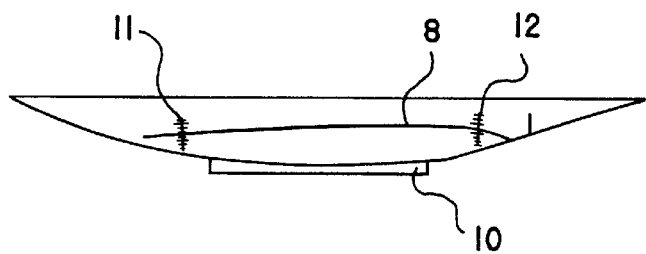
FIG. 6 is a side view, looking from the lateral side of the arch, of the convex Monson spherical plate having a dental arch chart drawn thereon, with the convex surface facing downwards.

Referring to FIGS.3 and 4, an arch 8 is drawn at a mid portion of a convex surface of a Monson spherical plate, while scales 11, 12 are drawn near the open end portion and closed (distal) end portion of the arch 8, respectively. An arch reference line 6 is drawn at a mid portion of the distal end of the arch 8 at right angles to the arch reference line 5 in registration with a tangential line of the arch 8 at the distal end thereof. In FIG. 4, an arch chart 8 is prepared and a portion 7 of the Monson spherical plate designed to be engaged by the anterior teeth is formed as a flat portion. As shown in FIG. 5, the flat portion 7 is designed for the anterior teeth and extends substantially horizontally with a sloped portion 7a connecting to the spherical portion. The sloped portion 7a is formed as a curved triangular slope.

Figure 7:
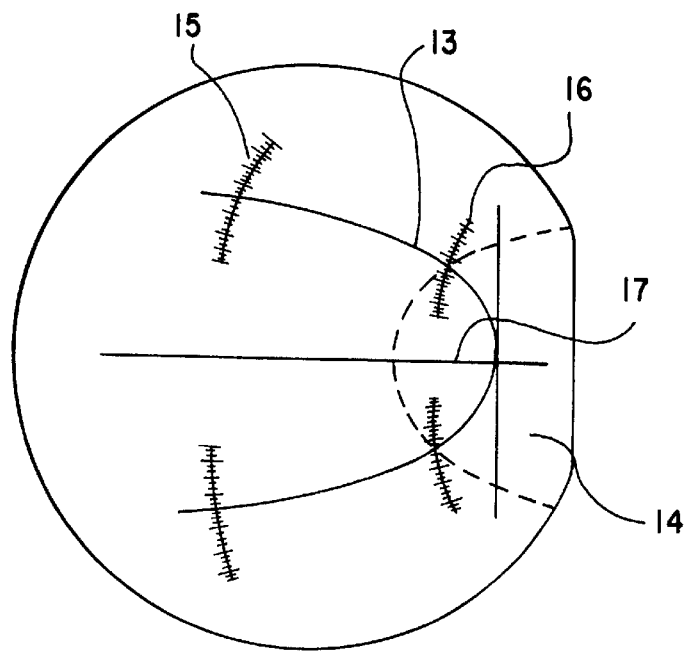
FIG. 7 is a top plan view of a concave Monson spherical plate, having a dental arch chart drawn thereon, according to another embodiment.

Referring to FIGS.7 and 8, the scales 15, 16, 23, 24 are drawn at points of intersection with the dental arches 13, 20 at left and right first molar teeth and at left and right canines, respectively, so that a tangential line drawn at the point of intersection will be substantially perpendicular to a tangential line drawn to the dental arch curve. This renders it possible to comprehend the direction and the amount of the movement of a constant point on the arch wire. Stated differently, a point on the arch wire is moved at all times along the scales. It is possible not to draw the mid portions of the scales, as shown.

It in noted that legs 9, 10 are provided between both sides of the arch curve 8 of the convex surface of the Monson spherical plate and an arch reference line 5. Meanwhile, the legs serve for preventing rolling of the spherical plate when the plate is placed and may depart from the shape shown. For example, small projections may be provided at respective apex points of a triangle.

The dental arch curves 1, 8 are curves extending along the outer side (buccal, labial side) of the dental arch. Typical of such arch may be a parabola a symmetrical axis of which passes through the center of a circle in a projection view of the Monson spherical plate when seen from the center of the Monson sphere. The dental arch curves are also curved even on a perspective plane including the axis of symmetry and which is perpendicular to the projected view (curve of Spee).

Meanwhile, if a Monson curve is afforded to an arch wire at the outset, such an arch wire may be exemplified which delineates a parabola, the axis of symmetry of which traverses the center of a circle in a projected drawing as seen from the center of sphere of the Monson spherical plate when the arch wire is set on the dental arch curve, with the wire being curved (curve of Spee) even on a plane containing the axis of symmetry and extending perpendicular to the plane of the projected drawing.

In the projected drawing as seen from the center of sphere of the Monson spherical plate, the scales 3, 11 include a straight line interconnecting the center points of the left and right first molar teeth, whilst the scales 4, 12 include a straight line interconnecting center points of the left and right canines. The curve representing the contour of the planar portions 2, 7 intersect the dental arch curves 1, 8 at the center points of at a median point between the left and right canines.

In the dental arch curves 1, 8 and in the scales 3, 4, 11 and 12, the standard size or the size associated with the individual difference, such as that due to the sex or race, may be depicted. In such case, those which give a size which fits on applying a dental pattern are selected. Alternatively, a dental pattern is applied to Monson spherical plate to determine the positions of the left and right first molar teeth, after which the sizes of the dental arch curves 1, 8 and the scales 3, 4, 11 and 12 are depicted. Since it suffices in such case if the reference tooth positions are specified, it is possible to omit the dental arch curves 1, 8 and even the scales 3, 4, 11 and 12.

Since it suffices if the positions of the teeth serving as a reference, in particular the first molar teeth and canines, are specified , the arch reference lines 5, 6 may be omitted and, if need be, any suitable marking may be used in their stead, even if arch charts are depicted in advance on the Monson spherical plate.

Theoretically, the Monson spherical plate is a portion of a spherical surface having a radius of curvature of approximately 10 cm (reference size). However, since the curve of the occlusal surface may differ with individuals, such as with sex or race, Monson spherical plates of variable sizes may be provided in order to meet such difference. Although the Monson spherical plate is formed of a material which keeps a pre-set shape, such as metal or transparent to semi-transparent plastics, it may also be formed of a deformable material, for such case wherein the Monson spherical plate has to adapt itself to variable actual occlusal surfaces to cope with individual differences.

In meeting with the size of the Monson spherical plate with variable radii of curvatures, arch wires, including those presenting Monson curves, may be fabricated with variable sizes to cope with mass production.

The arch wires may be of variable cross-sectional shapes, such as circular, square and rectangular cross-sectional shapes, if need be, and may be formed of those materials routinely used for dental use, such as shape memory alloys, enumerated by, for example, "true chrome" (stainless steel wire), "erdilloy wire" both manufactured by ROCKY MOUNTAIN MORITA CO. LTD., Japan "wallaby", "azloy", both manufactured by OHMCO CO. LTD., Japan "nai-tai" (nickel-titanium alloy), and "TMA" (titanium molybdenum alloy), both manufactured by OHMCO CO. LTD. The wire includes not only a single wire but also a multi-strand, braided wire made up of plural wires yarned together to present a rectangular cross-section, such as "fourth 9" manufactured by OHMCO CO. LTD., plural wires wound spirally about a core wire, and other sorts of wires that can be used for dental application. If shape memory alloys are used, the number of times of adjustment operations may be significantly decreased.

If the shape memory alloys are used, at least the curve corresponding to the Monson curve is to be memorized. As the memory shape, first or second shape (or more stages) may be memorized. For example, the first memory shape may be substantially coincident with the planar projection surface of the dental arch, whilst the second memory shape may be specified curved shape in meeting with the curved shape of the occlusal surface. Alternatively, the shape storage may occur in plural stages, such that deformation will occur to one or both of the different planar projection shape or different curve of occlusion. Other various storage forms or stages may also be used.

For shape memory, known means or other suitable means may be used in accordance with particular alloy characteristics.

On the Monson spherical plate, having an arch chart drawn thereon, a pattern of teeth, fabricated in accordance with a specified formula, is mounted so that the left and right first molar teeth and left and right canines are located at the points of intersection of the scales 3, 4, 11 and 12 with the dental arch curve. The arch wire is curved to follow up with the contour of the Monson curve and the contour of the dental arch curve, and the points traversed by the arch wire are inscribed on the scales 3, 4, 11, 12. This enables stepwise recognition of the amount of movement of the arch wire to the optimum position (target position) with lapse of time as from the time of mounting the arch wire to facilitate the compensating (correcting) operation. The arch wire may be mounted on the teeth by e.g., mounting a bracket on each tooth, the groove of which has an angle adapted to the curve of Spee, and by inserting the arch wire therein. If the arch wire is afforded in advance with the curve suited to the contour of the dental arch and the Monson curve, decision of the wire traversing point (start point) may be facilitated. Moreover, if the arch wire is formed of a shape memory alloy, arch wire exchange is almost dispended with, or the number of times of adjustment may be significanthy decreased.

If an arch chart is not drawn in advance on the Monson spherical plate (i.e., blank Monson spherical plate), a pattern of teeth, prepared by a known method, is placed(positioned) so that left and right canines are on a curve representing the contour of the planar portion. The positions of the left and right first molar teeth are specified and marks specifying these positions are stated on the Monson sphere. In this case, the blank Monson spherical plate should bear the scales and the arch reference line (or substitute marks). The subsequent process is similar to that when the arch chart is drawn in advance.

The meritorious effect of the present invention are summarized as follows.

The present invention, constructed as described above, has the following meritorious effects;

Since the Monson curve is applied to an arched arch wire to array the teeth, it is possible to prevent the Christensen phenomenon.

If the arch wire is used for correction, the teeth are not arrayed in planar shape, while smooth movement of the muscle around the jaw is not impeded due to the Monson curve.

Since the teeth are not arrayed in planar configuration, it is possible to apply a uniform compensating force to each tooth.

Since the scales are used in order to provide an even configuration in each step, the arch wire may be warped evenly. The arch wire interval (between two consecutive stages) can be correctly set in multiple stages in meeting to the progress of correction in each correction stage.

By curving the arch wire in meeting with the curve of the occlusal surface (Monson curve), adjustment of teeth on a pattern is facilitated. By forming the arch wire of shape memory alloys, arch wire exchange is almost dispensed with, while the adjustment frequency is reduced.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. A Monson spherical plate comprising a plate member having a partial Monson sphere wherein
    a dental arch curve configured for preparing an arch wire, scales and an arch reference line are drawn thereon for corrective full-band treatment.

2. The Monson spherical plate as defined in claim 1 wherein
    an arch chart comprising a maxillary dental arch curve, scales and an arch reference line is drawn in a concave surface of the Monson spherical plate and a portion thereof engaged by anterior teeth has a planar portion.

3. The Monson spherical plate as defined in claim 1 wherein
    an arch chart comprising a mandibular dental arch curve, scales and an arch reference line is drawn on a convex surface of the Monson spherical plate and a portion thereof engaged by the anterior teeth has a planar portion.

4. The Monson spherical plate as defined in claim 3 wherein
    legs are provided on the bottom of the Monson spherical plate.

5. The Monson spherical plate as defined in claim 1 wherein
    in a projection view as seen from a center of sphere of the Monson spherical plate said dental arch curve is formed by drawing a curve along a contour of an outer side (buccal, labial side) of the dental arch so that an axis of symmetry of the curve traverses the center of the Monson spherical plate.

6. The Monson spherical plate as defined in claim 1 wherein
    in a projection view as seen from a center of sphere of the Monson spherical plate, said arch reference line contains an axis of symmetry of the dental arch curve and a tangential line drawn to an apex point of the dental arch curve.

7. The Monson spherical plate as defined in claim 1 wherein
    in a projection view as seen from a center of sphere of the Monson spherical plate, said scales include a straight line interconnecting center points of left and right canines and a center point of the left and right first molar teeth.

8. The Monson spherical plate as defined in claim 1 wherein
    in a projection view as seen from a center of sphere of the Monson spherical plate, said planar portion has, as its contour, a curve an axis of symmetry of which coincides with the axis of the dental arch and the direction of which is opposite to that of the dental arch curve, with a point of intersection of said curve with the dental arch curve substantially coinciding with the position of left and right canines.

9. The Monson spherical plate as defined in claim 1 wherein said Monson spherical plate has a radius of curvature equal to a reference size or to a variety of sizes different therefrom.

10. A Monson spherical plate comprising a partial spherical surface corresponding to a curve of occlusion of a dental arch and scales configured for measuring the position of a dental arch curve or an arch wire depicted or placed thereon.

11. The Monson spherical plate as defined in claim 10 wherein
    at least a portion of the plate engaged by anterior teeth is formed as a planar portion.

12. The Monson spherical plate as defined in claim 11 having a dental arch curve and scales on one or both of concave and convex surfaces of said Monson spherical plate.

13. The Monson spherical plate as defined in claim 12 including an arch reference line constituting an axis of symmetry of said dental arch curve on one or both of concave and convex surfaces of said Monson spherical plate, said scales being formed so as to represent the lateral position of the dental arch curve.

14. The Monson spherical plate as defined in claim 1 wherein
   at a point of intersection of said scales with said dental arch curve at the left and right first molar teeth and left and right canines, a tangential line of said scales at said point of intersection is substantially perpendicular to a tangential line of said dental arch curve.

15. A method for preparing an arch wire comprising:
   providing said Monson spherical plate as defined in claim 1, and
   forming a curve of occlusion corresponding to said dental arch curve disposed on said Monson spherical plate in an arch wire.

16. An arch wire prepared by the method as defined in claim 15.

17. An arch wire having a planar projection shape substantially corresponding to a planar projection shape of a dental arch and a curve corresponding to the curve of occlusion of the dental arch defined by a partial spherical surface of a Monson spherical plate.

18. The arch wire as defined in claim 17 formed of a shape memory alloy.

* * * * *